United States Patent
Esselstein et al.

(10) Patent No.: US 6,638,267 B1
(45) Date of Patent: Oct. 28, 2003

(54) GUIDEWIRE WITH HYPOTUBE AND INTERNAL INSERT

(75) Inventors: Robert C. Esselstein, Fallbrook, CA (US); Brandon Gosiengfiao, Temecula, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 109 days.

(21) Appl. No.: 09/728,298

(22) Filed: Dec. 1, 2000

(51) Int. Cl.[7] .............................................. A61M 25/00
(52) U.S. Cl. ........................ 604/524; 604/247; 604/95
(58) Field of Search ........................ 604/247, 95, 102, 604/524, 530; 430/320; 600/585

(56) References Cited

U.S. PATENT DOCUMENTS

| | | | |
|---|---|---|---|
| 4,940,062 A | * | 7/1990 | Hampton et al. ............ 128/772 |
| RE34,466 E | | 12/1993 | Taylor et al. |
| 5,328,472 A | * | 7/1994 | Steinke et al. .............. 604/102 |
| 5,389,087 A | * | 2/1995 | Miraki ....................... 604/247 |
| 5,480,382 A | | 1/1996 | Hammerslag et al. ......... 604/95 |
| 5,549,556 A | * | 8/1996 | Ndondo-Lay et al. ....... 604/102 |
| 5,741,429 A | | 4/1998 | Donadio, III et al. .......... 216/8 |
| 5,820,571 A | | 10/1998 | Erades et al. ............... 600/585 |
| 6,027,863 A | | 2/2000 | Donadio, III ............... 430/320 |
| 6,068,623 A | | 5/2000 | Zadno-Azizi et al. ........ 604/530 |
| 6,217,567 B1 | | 4/2001 | Zadno-Azizi et al. ........ 604/530 |

* cited by examiner

*Primary Examiner*—Henry Bennett
*Assistant Examiner*—Sabrina Dagostino
(74) *Attorney, Agent, or Firm*—Fulwider Patton Lee & Utecht, LLP

(57) ABSTRACT

A guidewire having a proximal hypotube portion with an insert to increase pushability and torqueability. The insert may comprise metals such as stainless steel, shape memory/super elastic materials such as nickel titanium alloys, composite materials or polymeric materials. The proximal end of the insert may be configured to dock with an extension guidewire. Preferably, the proximal end of the solid core distal portion of the guidewire is configured to fit within the hypotube and the two are secured by adhesive, solder or the like.

20 Claims, 2 Drawing Sheets

GUIDEWIRE WITH HYPOTUBE AND INTERNAL INSERT

BACKGROUND OF THE INVENTION

Elongated guiding members are widely used in medical procedures. A common example are the guidewires used to locate intravascular devices such as angioplasty catheters. Since guidewires must traverse the peripheral and tortuous coronary in order to reach the desired treatment location, they must exhibit a number of important characteristics. Specifically, a guidewire should have sufficient strength and elasticity to impart suitable pushability, trackability, torqueability, flexibility and handleability.

It has proven challenging to maximize these functional characteristics while maintaining the necessary overall dimensions. One prior art guidewire design utilizes a proximal hypotube portion. Although this design offers advantages, it also suffers from certain drawbacks. Most significantly, the use of a hypotube increases the chance the guidewire will kink as it is being advanced within the vasculature or through a guiding catheter. In addition, due to the reduced cross sectional area relative to a solid wire of the same outer diameter, such hypotube guidewires generally suffer from similarly reduced torqueability.

Thus, there is a need for an elongated guiding member with a proximal hypotube portion having improved performance characteristics. Specifically, there is a need for a hypotube guidewire with enhanced pushability that reduces the chance of kinking. There is also a need for a guidewire with a proximal hypotube shaft that transmits torque more efficiently than conventional guidewires formed from a hypotube. This invention satisfies these and other needs.

SUMMARY OF THE INVENTION

The invention is directed to an elongated guiding member for medical devices such as a guidewire having an elongated proximal hypotube portion with an internal insert disposed within the interior hypotube and a relatively short solid core distal portion. The insert may be composed of metals such as stainless steel, shape memory/superelastic materials such as nickel-titanium alloys, composite materials or polymeric materials. Preferably, the solid distal core portion has a swaged or plunge ground proximal end that may be inserted into the distal end of the proximal hypotube portion. The proximal and distal core portions are secured by mechanical means or by adhesive, solder, brazing, welding or other suitable means. The proximal hypotube portion of the guiding members of the invention preferably are provide with a low friction coating.

In certain embodiments, the proximal end of the hypotube insert is configured to allow convenient attachment to other members, such as extension wires. For example, the proximal end of the hypotube insert may be swaged, coined or plunge ground to allow member to be attached to be easily docked with the proximal end of the hypotube insert which extends out the proximal end of the hypotube. The hypotube insert is also preferably configured to be removable, allowing the user to select from a variety of inserts and thus tailor the performance characteristics of the guidewire to suit the procedure. These and other advantages of the invention will become more apparent from the following detailed description of the invention and the accompanying exemplary drawings. n

DETAILED DESCRIPTION OF THE INVENTION

Figure 1:
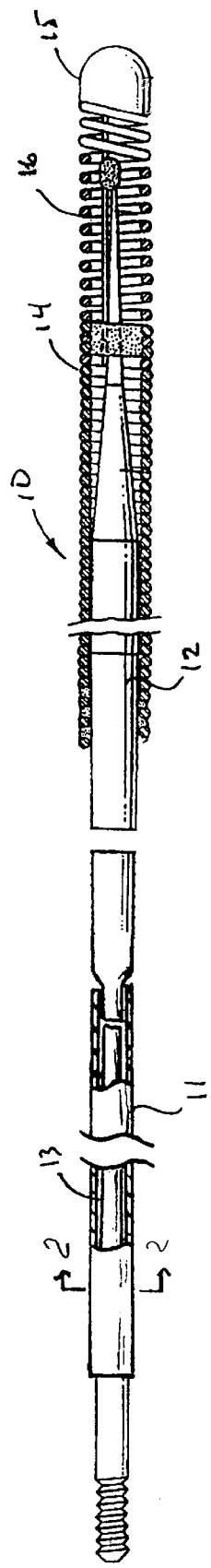
FIG. 1 is schematic view, partially in section, of a guidewire embodying features of the invention.
Figure 2:
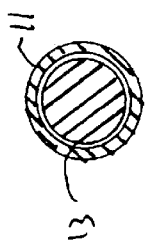
FIG. 2 is an cross sectional view of the guidewire from FIG. 1, taken at 2—2, showing the proximal hypotube portion with an insert.

FIG. 1 illustrates a guidewire 10 embodying features of the invention that is adapted to be inserted into a patient's body lumen, such as an artery. The guidewire 10 comprises an elongated, proximal hypotube portion 11 and a relatively short distal portion 12. As shown more clearly in FIG. 2, an insert 13 is disposed within proximal hypotube portion 11. The proximal end of distal portion 12 is configured to permit insertion into the distal end of hypotube 11. Generally, the proximal end of distal portion 12 is plunge ground or swaged so that it has an outer diameter that will fit within the distal end of hypotube 11. The ends may be press fit, secured by crimping or swaging or by means such as a suitable adhesive or by welding, brazing or soldering.

A helical coil 14 is disposed about the distal portion 12 and has a rounded plug 15 on the distal end thereof. The coil 14 is secured to the distal portion 12 at proximal location and at intermediate location by a suitable solder. A shaping ribbon 16 is secured by its proximal end to the distal portion 12 and by the distal end thereof to the rounded plug 15 which is usually formed by soldering or welding the distal end of the coil 14 to the distal tip of the shaping ribbon 16. Alternatively, the distal end of the core member may be flattened and secured to the coil. Preferably, the most distal section of the helical coil 14 is made of radiopaque metal such as platinum or platinum-nickel alloys to facilitate the fluoroscopic observation while it is disposed within a patient's body.

Insert 13 may comprise virtually any solid material, but preferably is composed of metals such as stainless steel, shape memory/superelastic materials such as nickel-titanium alloys, composite materials or polymeric materials. Insert 13 provides additional structure to hypotube 11, helping to prevent kinking as guidewire is advanced though a patient's vasculature. Further, insert 13 can increase the stiffness of hypotube 11 to improve the pushability of the guidewire. Insert 13 may also be used to increase the torqueability of the guidewire. Preferably, insert 13 is removable/exchangeable, allowing the user to select an insert having the desired stiffness to tailor the performance characteristics of the guidewire.

Distal portion 12 and hypotube 11 are preferably formed from metals such as stainless steel or shape memory/superelastic materials such as nickel-titanium alloys. Preferably, hypotube 11 is coated with a lubricous coating to facilitate travel within a catheter or a bodily lumen. Suitable coatings include polytetrafluoroethylene (sold under the trademark Teflon by du Pont, de Nemours & Co.), polysiloxane and the like.

Figure 3:
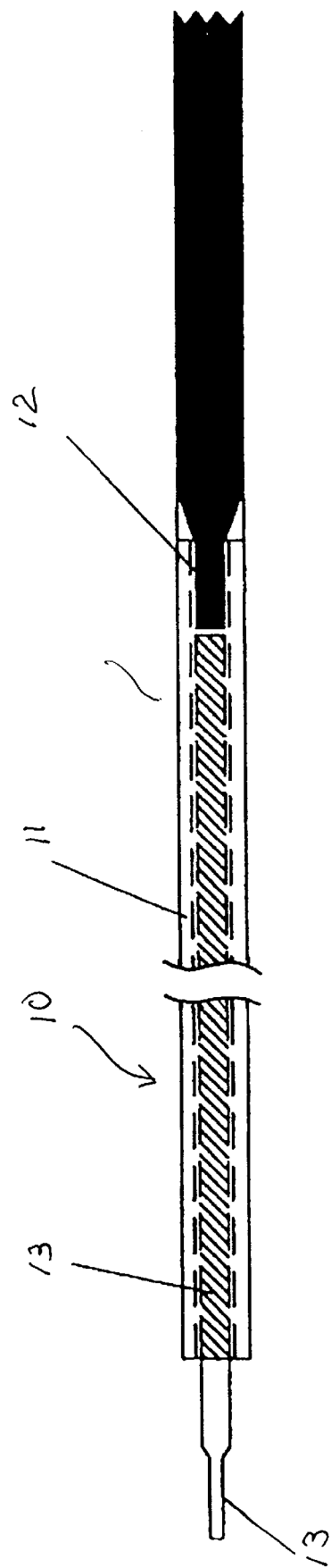
FIG. 3 is a partial schematic view of a guidewire embodying features of the invention, showing a hypotube insert with a tapered proximal end suitable for connection with another elongated member.

In some embodiments, such as the ones shown in FIGS. 1 and 3, the proximal end of insert 13 is configured to connect with another medical device. The end may be plunge ground, swaged, coined or the like to permit easy docking with a guidewire extension device or other suitable medical device.

The proximal hypotube portion 11 of the guidewire 10 is generally about 145 cm to about 300 cm in length with an outer diameter of about 0.01 to 0.018 inch (0.25–0.46 mm), preferably about 0.012 to 0.014 inch (0.31–0.46 mm) including the lubricous coating. Larger diameter guidewires may be employed in peripheral arteries and other body lumens. Generally, the insert 13 should have a length approximately the same as the hypotube, with additional length at the proximal end to allow swaging, plunge grinding, coining and the like to allow for extension wire docking. The inner diameter of hypotube 11 should be about 0.005 to about 0.012 inch (0.13–31 mm) and the insert 13 outside diameter should correspondingly be from about 0.005 to about 0.011 inch (0.13–0.28 mm). The helical coil 14 is about 20 to about 45 cm in length, has an outer diameter about the same size as the diameter of the elongated proximal portion 11, and is made from wire about 0.002 to 0.003 inch (0.051–0.076 mm) in diameter.

Described herein are preferred embodiments, however, one skilled in the art that pertains to the present invention will understand that there are equivalent alternative embodiments. Although the described embodiments have comprised guidewires, the invention can be used to create other solid, elongated, small diameter medical devices from two or more discrete sections. For example, devices such as pacing leads may be formed using the methods disclosed herein.

What is claimed is:

1. An elongated guiding member for medical procedures comprising an elongated proximal hypotube portion with an insert disposed within an interior of the hypotube portion and a solid core distal portion fixedly secured to a distal end of the hypotube.

2. The elongated guiding member of claim 1, wherein the insert comprises stainless steel.

3. The elongated guiding member of claim 1, wherein the insert comprises a nickel-titanium alloy.

4. The elongated guiding member of claim 1, wherein the insert comprises a composite material.

5. The elongated guiding member of claim 1, wherein the insert comprises a polymeric material.

6. The elongated guiding member of claim 1, wherein the distal portion has a proximal end that is configured to fit within a distal end of the proximal hypotube.

7. The elongated guiding member of claim 6, wherein the proximal end of the distal portion is secured to the distal end of the proximal hypotube by mechanical means.

8. The elongated guiding member of claim 6, wherein the proximal end of the distal portion is secured to the distal end of the proximal hypotube by solder.

9. The elongated guiding member of claim 6, wherein the proximal end of the distal portion is secured to the distal end of the proximal hypotube by adhesive.

10. The elongated guiding member of claim 1, wherein a proximal end of the insert is configured to dock with a medical device.

11. The elongated guiding member of claim 10, wherein the proximal end of the insert is configured to dock with an extension guidewire device.

12. The elongated guiding member of claim 1, wherein the proximal hypotube is coated with a lubricous material.

13. The elongated guiding member of claim 12, wherein the lubricous material comprises polytetrafluoroethylene.

14. The elongated guiding member of claim 1, wherein the insert is removable.

15. The elongated guiding member of claim 1, wherein the insert is configured to increase the pushability of the guidewire.

16. The elongated guiding member of claim 1, wherein the insert is configured to increase the torqueability of the guidewire.

17. A guide wire comprising:

a hypotube having an interior, a proximal end and a distal end;

a solid core distal portion having a distal end and a proximal end secured to the distal end of the hypotube; and an insert partially disposed within the interior of the hypotube, wherein the insert is removable from the interior of the hypotube.

18. The guide wire of claim 17, wherein the proximal end of the distal portion is configured to fit within the distal end of the hypotube.

19. The guide wire of claim 17, wherein the insert has a proximal end extending out of the interior of the hypotube, the proximal end of the insert being configured for docking with an extension guidewire device.

20. The guide wire of claim 17, wherein a helical coil is attached to the distal end of the distal portion.

* * * * *